(12) United States Patent
Causevic

(10) Patent No.: US 8,579,812 B2
(45) Date of Patent: Nov. 12, 2013

(54) SYSTEM AND METHODS FOR MANAGEMENT OF DISEASE OVER TIME

(75) Inventor: Elvir Causevic, Clayton, MO (US)

(73) Assignee: Brainscope Company, Inc., Bethesda, MD (US)

( * ) Notice: Subject to any disclaimer, the term of this patent is extended or adjusted under 35 U.S.C. 154(b) by 613 days.

(21) Appl. No.: 12/638,602

(22) Filed: Dec. 15, 2009

(65) Prior Publication Data

US 2011/0144518 A1 Jun. 16, 2011

(51) Int. Cl.
*A61B 5/00* (2006.01)

(52) U.S. Cl.
USPC .......................................... 600/300; 600/544

(58) Field of Classification Search
USPC ................................................ 600/300, 544
See application file for complete search history.

(56) References Cited

U.S. PATENT DOCUMENTS

| | | | |
|---|---|---|---|
| 4,928,704 A | 5/1990 | Hardt | |
| 6,622,036 B1 | 9/2003 | Suffin | |
| 6,866,639 B2 | 3/2005 | Causevic et al. | |
| 6,974,421 B1 | 12/2005 | Causevic et al. | |
| 7,054,453 B2 | 5/2006 | Causevic et al. | |
| 7,123,955 B1 | 10/2006 | Gao et al. | |
| 7,187,790 B2 | 3/2007 | Sabol et al. | |
| 7,256,708 B2 | 8/2007 | Rosenfeld et al. | |
| 7,321,862 B2 | 1/2008 | Rosenfeld et al. | |
| 7,343,197 B2* | 3/2008 | Shusterman | 600/509 |
| 7,490,085 B2 | 2/2009 | Walker et al. | |
| 7,720,530 B2* | 5/2010 | Causevic | 600/544 |
| 2002/0091335 A1 | 7/2002 | John et al. | |
| 2002/0188217 A1 | 12/2002 | Farwell | |

(Continued)

FOREIGN PATENT DOCUMENTS

| | | |
|---|---|---|
| EP | 1 541 082 A1 | 6/2005 |
| GB | 2 437 106 A | 10/2007 |

(Continued)

OTHER PUBLICATIONS

Co-Pending U.S. Appl. No. 12/615,423, filed Nov. 10, 2009.

(Continued)

*Primary Examiner* — Navin Natnithithadha
*Assistant Examiner* — Etsub Berhanu
(74) *Attorney, Agent, or Firm* — Finnegan, Henderson, Farabow, Garrett & Dunner LLP

(57) ABSTRACT

A system for delivering health information is provided. The system comprises at least one apparatus configured to receive information related to a condition of a patient. The analysis system further comprises a reception system configured to receive data related to the patient's condition and a processor configured to assess a condition of a patient and to identify a data set including information related to the patient's condition. The system also comprises a communication system configured to communicate the data set to a user.

17 Claims, 8 Drawing Sheets

(56) References Cited

U.S. PATENT DOCUMENTS

| | | |
|---|---|---|
| 2003/0135128 A1* | 7/2003 | Suffin et al. .................... 600/544 |
| 2003/0139684 A1 | 7/2003 | Thornton |
| 2003/0225340 A1 | 12/2003 | Collura |
| 2004/0015337 A1 | 1/2004 | Thomas et al. |
| 2004/0122719 A1 | 6/2004 | Sabol et al. |
| 2004/0122790 A1 | 6/2004 | Walker et al. |
| 2004/0172305 A1 | 9/2004 | Soerensen |
| 2006/0153396 A1 | 7/2006 | John |
| 2006/0241697 A1 | 10/2006 | Libbus et al. |
| 2007/0016046 A1* | 1/2007 | Mozayeni et al. ............ 600/443 |
| 2007/0032737 A1 | 2/2007 | Causevic et al. |
| 2007/0106169 A1 | 5/2007 | Fadem |
| 2007/0118399 A1 | 5/2007 | Avinash et al. |
| 2007/0167691 A1* | 7/2007 | Causevic ..................... 600/301 |
| 2007/0244724 A1* | 10/2007 | Pendergast et al. ............... 705/3 |
| 2008/0004904 A1 | 1/2008 | Tran |
| 2008/0125669 A1 | 5/2008 | Suffin |
| 2008/0208073 A1 | 8/2008 | Causevic |
| 2008/0228522 A1 | 9/2008 | Davis et al. |
| 2009/0105785 A1 | 4/2009 | Wei et al. |
| 2009/0220429 A1 | 9/2009 | Johnsen et al. |
| 2009/0247894 A1* | 10/2009 | Causevic ..................... 600/544 |
| 2009/0264785 A1 | 10/2009 | Causevic |
| 2010/0143256 A1* | 6/2010 | Suffin et al. .................... 424/9.2 |
| 2011/0087125 A1* | 4/2011 | Causevic ..................... 600/544 |
| 2011/0112426 A1* | 5/2011 | Causevic ..................... 600/544 |
| 2011/0144519 A1* | 6/2011 | Causevic ..................... 600/544 |
| 2011/0144520 A1* | 6/2011 | Causevic et al. .............. 600/544 |

FOREIGN PATENT DOCUMENTS

| | | |
|---|---|---|
| WO | WO 00/16690 | 3/2000 |
| WO | WO 00/35344 | 6/2000 |
| WO | WO 02/098291 A2 | 12/2002 |
| WO | WO 2005/072459 A2 | 8/2005 |
| WO | WO 2005/072608 A1 | 8/2005 |
| WO | WO 2006/034024 A2 | 3/2006 |
| WO | WO 2007/140535 | 12/2007 |
| WO | WO 2008/148894 A1 | 12/2008 |
| WO | WO 2009/045449 A1 | 4/2009 |
| WO | WO 2009134475 A1 * | 11/2009 |

OTHER PUBLICATIONS

Co-pending U.S. Appl. No. 12/639,218, filed Dec. 16, 2009.
PCT International Search Report and Written Opinion mailed Jan. 28, 2011, in PCT/US2010/055954.
PCT International Search Report and Written Opinion mailed Mar. 25, 2011, in PCT/US2010/060182.
PCT International Search Report and Written Opinion mailed Mar. 3, 2011, in PCT/US2010/059836.

* cited by examiner

SYSTEM AND METHODS FOR MANAGEMENT OF DISEASE OVER TIME

FIELD

The present disclosure pertains to devices and methods for managing a patient's disease state, and in particular, to systems and methods for providing information to patients and those involved in their treatment over the course of a patient's condition.

BACKGROUND

Many important health conditions have prolonged disease courses. In addition, the type of health information that is most interesting or valuable for a patient at the time of diagnosis is often very different from the type of information needed at various stages of disease progression. Further, coordination of delivery of health information can be complicated by variations in disease progression and/or development of patient-specific complications or other factors. Therefore, to provide appropriate health information, it would be desirable to have systems that allow assessment of a patient's disease state or disease progression and provide health information related to a patient-specific assessment at a particular disease stage.

It is accordingly an object of the systems and methods of the present disclosure to provide systems and methods to assess a patient's condition and to provide timely information to the patient based on their current condition and disease progression.

SUMMARY

A system for delivering health information is provided. The system comprises at least one apparatus configured to receive information related to a condition of a patient. The system further comprises an analysis system. The analysis system comprises a reception system configured to receive data related to the patient's condition and a processor configured to assess a condition of a patient and to identify a data set including information related to the patient's condition. The system also comprises a communication system configured to communicate the data set to a user.

A method for communicating health information is provided. The method comprises collecting information related to the condition of a patient and entering the information related to the condition of a patient in a computerized data collection system. The information is to an analysis system configured to process the information to assess a disease stage of the patient, identify a data set including information related to the patient's condition, and communicate the data set to a user.

A system for delivering health information is provided. The system can comprise at least one reception device configured to receive information related to a condition of a patient; an analysis system including a receiver configured to receive data related to the patient's condition and a processor circuit configured to process data related to the patient's condition, to determine a distinct stage of progression of the patient's condition, and to identify a data set based on the patient's condition; and a communication system configured to communicate the data set.

DESCRIPTION OF EXEMPLARY EMBODIMENTS

Figure 1:
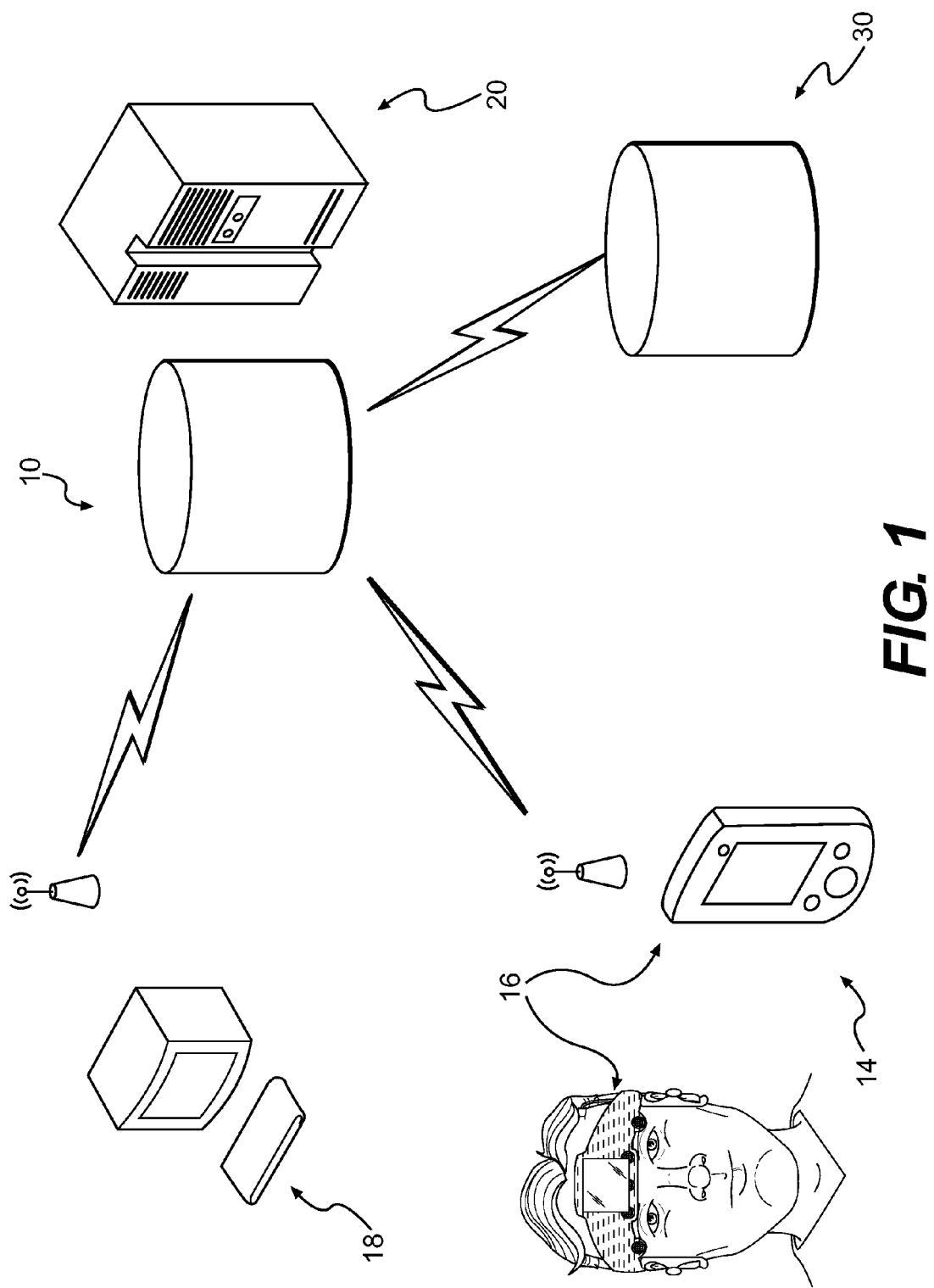
FIG. 1 illustrates a system for delivering healthcare information, according to certain exemplary embodiments.

Reference will now be made in detail to exemplary embodiments according to the present disclosure, examples of which are illustrated in the accompanying drawings. Wherever possible, the same reference numbers will be used throughout the drawings to refer to the same or like parts.

The present disclosure pertains to systems and methods for facilitating the timely and disease-stage dependent distribution of health information. In some embodiments, the system can be used to distribute information related to a treatment recommendation, types of care, support provisions, financing of healthcare, health maintenance, prevention of complications, medication side effects, and/or any other health information that may be of time-specific interest to a patient or other persons involved in the care of a patient. In some embodiments, the health information can be communicated to the patient or others over the time course of a patient's disease. Further, in some embodiments, the system and methods of the present disclosure can facilitate monitoring of the progression or stabilization of a patient's disease. In some embodiments, the systems of the present disclosure will assist in distributing timely healthcare information to the patient as their disease or condition develops. In some embodiments, the systems will provide advance information about likely upcoming disease states or stages, and information relevant to the next or following stages of disease.

Access to timely medical information is important for patients, medical professionals, and others involved with the care and treatment of acutely or chronically ill patients. Coordinating delivery of appropriate information to assist in treatment and lifestyle planning, to provide emotional support, or otherwise assist in patient decision-making and understanding can be difficult, and improved systems and methods for providing appropriately timed information to patients are needed. The main obstacles today are either an absence of suitable information, or on the other hand information overload, as all available information is presented to the patient and their environment at the same time. This is not effective or efficient. As patients pass through many distinct disease stages, it is most effective to provide information to them about the exact stage they are in, and the immediately following stage so they can prepare for upcoming events.

Generally, information related to diseases and treatment options is provided by a limited number of individuals whose interests may be related to only one or two facets of a disease process. For example, physicians and other medical professionals are generally focused on treating disease causes or managing symptoms, and often do not have the time or motivation to address nonmedical concerns sufficiently. In addition, peer support groups or information sources (e.g., web blogs and literature) are limited to the experience and knowledge of the group members, may not be available to or desirable for some patients, and cannot assess each patient's medical issues precisely. Further, family and friends are inherently biased in providing information and advice to patients, and, therefore, are not always a reliable source of information.

Conversely, medical information systems, including medical databases and data networks have been developed primarily to assist in storing and communicating medical record data to assist in prescribing and controlling medical resources. In addition, remote patient monitoring systems have been developed that allow continuous or periodic monitoring and collection of patient health information, while facilitating communication between patients and health care professionals. However, there remains a need for systems for assessing the time course of a patient's disease or condition and providing timely information related to available diagnostics, recommended to possible treatments, lifestyle issues, finances, and numerous other issues affecting patients.

The systems and methods of the present disclosure may include one or more systems or devices for receiving information related to the condition of a patient. As described in more detail below, the systems or devices can include numerous different health information input systems and/or diagnostic apparatuses that are configured to receive information related to a disease or condition of a patient. In some embodiments, these devices and systems can be designed to specifically collect information related to the condition of a patient in order to assess the time status of a patient's disease. In other embodiments, these devices or apparatuses can be designed for other specific or general healthcare purposes, but can include components that allow recording and/or transfer of information related to the patient's condition or disease. Further, in some embodiments, as described in more detail below, the systems and methods of the present disclosure can employ multiple apparatuses or devices for collecting healthcare information and can be distributed as a network of devices that are configured to receive information related to a patient's condition or disease.

FIG. 1 illustrates a system for delivering healthcare information 10, according to certain embodiments of the present disclosure. As shown, the system 10 can include one or more reception devices 14, 18 configured to receive information about the condition of a patient. The devices 14,18 are configured to transmit the data related to the condition of a patient to an analysis system 20, which can include a database and processor system. The analysis system 20, as described in more detail below, can include a reception system configured to receive data about the patient's condition and a processor configured to assess the condition of a patient and to identify a data set including information related to the patient's condition. In addition, in some embodiments, the analysis system 20 can be connected to one or more communication systems 30 configured to communicate information related to the data set to a patient or other person or persons involved in the care of a patient.

In some embodiments, the system 10 can include two or more reception devices 14,18. The receptions devices 14,18 can include any type of medical process information receiving system configured to receive diagnostic or other healthcare information related to a patient's condition. In addition, the system 10 can include multiple reception devices distributed at various locations and configured to receive information about the same patient or about multiple different patients. Furthermore, the reception devices 14,18 can be located at doctor's offices, at any other point-of-care location, at a patient's home, or at consumer or retail locations such as pharmacies, shopping centers, or any other location where it may be convenient to collect information related to the condition of a patient.

In some embodiments, at least one reception device 14 can be configured to collect information directly from the patient pertaining to the patient's condition. For example, as shown in FIG. 1, the reception device 14 can include a patient interface and transponder system 16. As shown, the interface and transponder system 16 is configured to collect information related to a patient's brain electrical activity. In some embodiments, the system 16 can include a brain electrical monitoring system including one or more electrodes configured to sense brain electrical activity. However, it will be appreciated that other types of patient interfaces can be used that are configured to collect information directly from a patient. Such systems can include, for example, blood pressure monitors, other cardiovascular monitors, glucose monitors, or other systems configured to collect diagnostic and physiologic information from a patient.

In addition, as shown in FIG. 1, the second reception device 18 can include systems configured to receive information provided or input by a user. In some embodiments, such systems can include data entry interfaces, such as, for example, computer terminals, as shown in FIG. 1, configured to receive information input by healthcare personnel, patients, or others involved in the care or monitoring of patients. Further, it will be appreciated that combinations of direct patient monitors and patient data input systems can be used to facilitate accurate and timely monitoring of a patient's condition and the time status of a patient's disease.

In addition, the reception devices, such as the patient data input system 18, can be configured to interface with or receive information from other medical records systems. In some embodiments, the medical records systems can include, for example, hospital medical records, laboratory records, radiologic records, and/or any other data storage media. Further, it will be understood that the reception devices 14, 18 can be distributed at various locations to collect information from different personnel involved in the care of a patient or directly from a patient, or can be contained at a single common location.

In some embodiments, the reception devices 14,18 are configured to transmit information to the analysis system 20 for processing and identification of a data set related to a patient's condition. Any suitable communication system can be used to allow communication between the reception devices 14,18 and the analysis system 20. For example, as shown, the reception devices 14,18 can include wireless transponders configured to transmit data through a wireless connection to the analysis system 20. However, in some embodiments, other types of data connections can be used. For example, other connections can include internet connections, telephone connections, direct wire links in healthcare facilities, and other suitable connection types. In addition, different types of data connections can be used for different types of receiver devices and analysis systems. For example, some patient monitoring systems may include wireless data connections that are configured to monitor patient physiologic conditions directly. In addition, some patient data information input systems can include static connections, as for example, connections at a doctor's office or other healthcare facility, and such static connections may be configured to transmit information over a landline or telephone connection.

In addition, reception devices 14, 18 can be contained within a common unit or device, or near, analysis system 20.

Accordingly, reception devices 14, 18 can communicate through simple wired connections to feed information directly to analysis system 20. This may be the case, for example, where a single device is used repeatedly, e.g., with a single device owned by a user such as a patient, doctor's office, or other point-of care setting.

According to certain embodiments of the present disclosure, the system 10 can include a distributed network of devices including reception devices 14, 18 and analysis systems 20. Accordingly, the analysis system 20 can be located at a location distant from one or more reception devices 14,18. Further, in some embodiments, the analysis system 20 can be located at the same location as one or more reception devices 14, 18 and distant from additional reception devices. In addition, multiple analysis systems 20 can be included in an integrated network of reception devices and analysis systems.

In some embodiments, the analysis system 20 can be configured to identify a data set to be communicated to a patient or others involved in the care of a patient. As described in more detail below, the data set can be related to a patient's condition and can be specifically selected based on the time status of a patient's specific condition. Further, in some embodiments, the data set can be selected based on classification of the patient's condition and the time status of the patient's condition. In some embodiments, the classification of the condition and the time status can be based on a comparison with the condition and time status of other groups of patients stored in a database. As described in more detail below, the data set may be selected based on factors specific to a patient's disease or condition including, for example, the stage or severity of a disease, presence of comorbid conditions, prescription drug use, drug side effects, financial factors, family support factors, genetic variables, and/or any other factor influencing information that may be useful or interesting to patients or others involved in the care of a patient.

As indicated in FIG. 1, a selected data set can be communicated to a communication system 30 for use by patients or others involved in the care of a patient. As described in more detail below, the communication system 30 can include visual, auditory, and/or other communications systems. In some embodiments, the communication system 30 can include web or internet-based systems, television programs, any form of audio visual media, books, mail order systems, and/or other types of information. Further, the communication system 30 can be selected based on specific patient preferences, specific patient diseases or conditions, and the ability of patients or others receiving the information to interact with various types of communication media.

Figure 2:
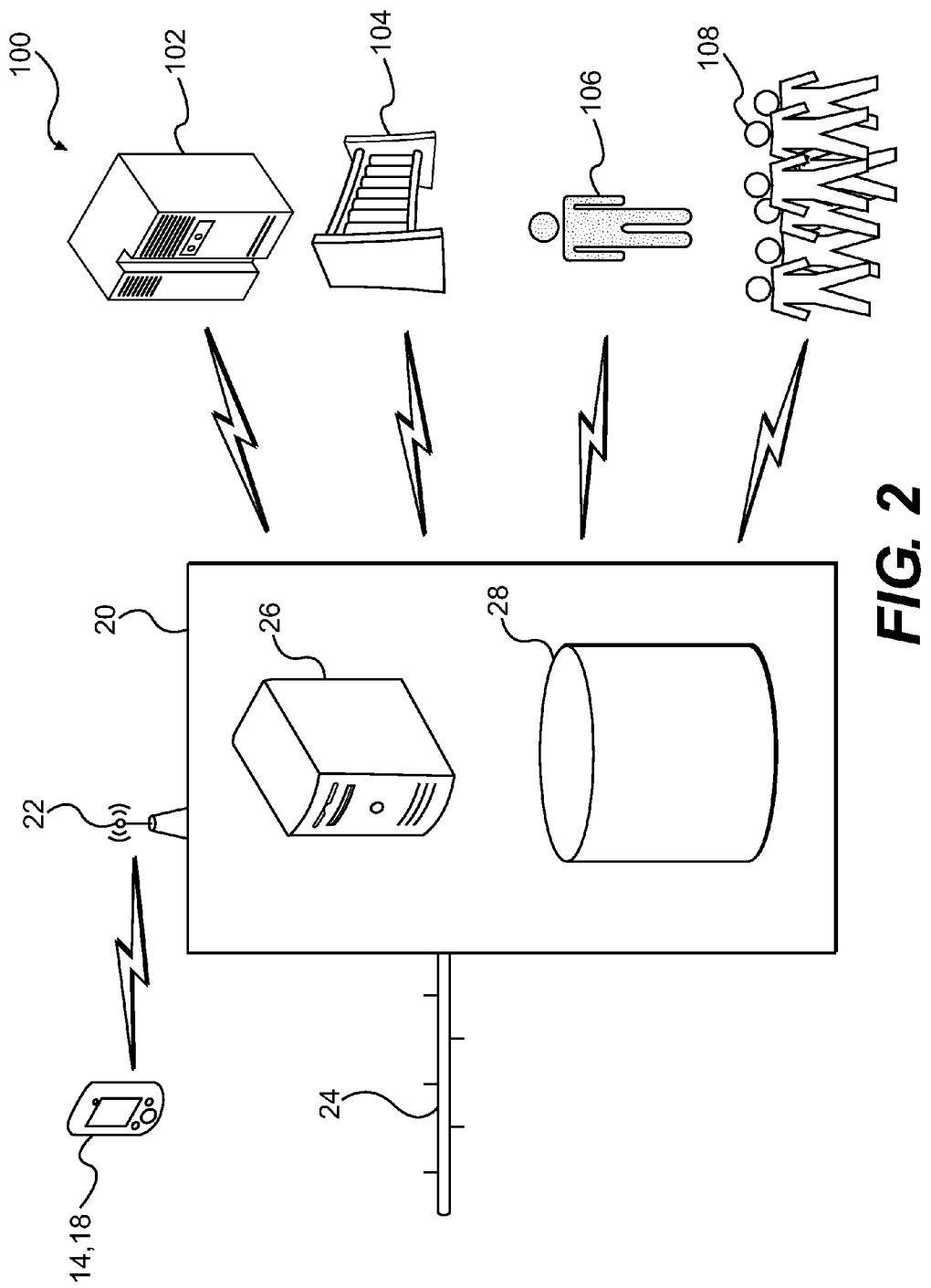
FIG. 2 illustrates an analysis system for assessing a patient's condition, according to certain embodiments of the present disclosure.

FIG. 2 illustrates a more detailed view of an analysis system 20, according to certain embodiments of the present disclosure. As shown, the analysis system 20, can be configured to interface with one or more reception devices 14, 18 and to receive information from the reception devices 14, 18. Further, as noted above, the analysis system 20 can be configured to include both wireless connections 22 and hardwired connections 24 to communicate with reception devices 14, 18 and other devices to receive information related to patient data sets. Further, in some embodiments, the analysis system 20 can include a processor system 26 and a database 28 that contains information related to patient conditions. In some embodiments, the database 28 can include a set of information that may be useful to patients based on the specific patient disease or condition and the time status of a patient's disease, and such information can be selected to be communicated to patients or others throughout the time course of the patient's disease to assist in the education, care, and support of those patients throughout the time course of the patient's disease.

In some embodiments, the processor system 26 can include an automatic, computerized processor system configured to receive information related to a patient's condition or disease and to process such information to assist in selection of a data set related to the patient's condition. A variety of suitable computerized processor systems 26 may be selected, and the specific computerized processor system will be selected based on the volume of use, cost, and the specific diseases or conditions that may be analyzed.

In some embodiments, the processor system 26 may be configured to receive raw data related to patient diseases or conditions. In certain embodiments, the processor system 26 may process the raw data to identify a specific patient disease or condition, as described in more detail below. In certain embodiments, the processor system 26 may be configured to receive a final disease condition or status as determined by other processor systems, or as analyzed by reception devices 14,18. Further, in some embodiments, the reception devices 14, 18 may perform analysis prior to sending data to the processor system 26, and the processor system 26 may perform analysis on data received from the reception devices 14, 18.

As noted above, the database 28 can include information related to various patient diseases or conditions and the time status of patient diseases. In addition, the database can store information related to the care of patients, as well as information that may be of interest to patients or others involved in patient care. As described in more detail below, the processor system 26 can select a patient data set contained in the database 28 based on the patient disease or condition and time status of the patient disease or condition. Further, the database 28 can be contained at the same location as one or more processor systems 26 or can be part of a distributed network of processor systems and databases. In some embodiments, multiple databases 28 can be included. For example, some databases may contain information related to specific patient diseases or conditions and/or the time status of that patient's disease. These databases 28 can be used to select a particular patient condition and time status that may further be used to select a particular data set of interest to the patient or others involved in the care of a patient. In some embodiments, additional databases may include information related to the care of patients suffering from other diseases and/or having various time statuses.

As shown in FIG. 2, the analysis system 20, including the processor system 26 and database 28, can be connected to various other information sources 100. These other information sources 100 can communicate with the processor 26 and/or database 28 to allow information stored in the database 28 to be updated and/or to update algorithms within the processor 26 for identifying a patient's disease or condition and/or time status. As noted previously, these additional data sources 100 can include other processors or databases 102. These other processors or databases 102 can perform similar processing and data storage functions as those contained in the analysis system 20. In some embodiments, the other processors or databases 102 can include any type of electronic media storage including other data storage systems or other media interfaces configured to communicate with the analysis system 20.

In addition, additional data sources 100 can include other information repositories, various healthcare workers, and patient support groups. For example, as shown, in some embodiments, any type of patient information library 104 can be configured to communicate with the processor system 26 and/or database 28 to update the information stored therein, thereby allowing the information from which the dataset to be communicated to the patient or others to be expanded or updated as new information becomes available. In addition, in some embodiments, various healthcare personnel 106, including doctors, nurses, social workers, or any other healthcare personnel interested in the care of patients with various diseases or conditions may communicate with the database 28 to access and/or update the information stored therein. Further, various peer support groups 108, including support groups involved in the care and dissemination of information to patients, may be able to communicate with the database 28 in order to access and/or update the information stored therein. Such groups may include various peer support groups or societies interested in certain diseases or conditions including those interested in chronic diseases or very rare diseases. Since support groups may provide disease-specific information, but may also provide information related to resources for support with social issues related to various diseases or conditions, these groups can provide information related to any facet of a disease or condition that may affect a person's life, thereby allowing additional patient information related the specific disease or condition over the time course of a patient's disease.

Figure 3:
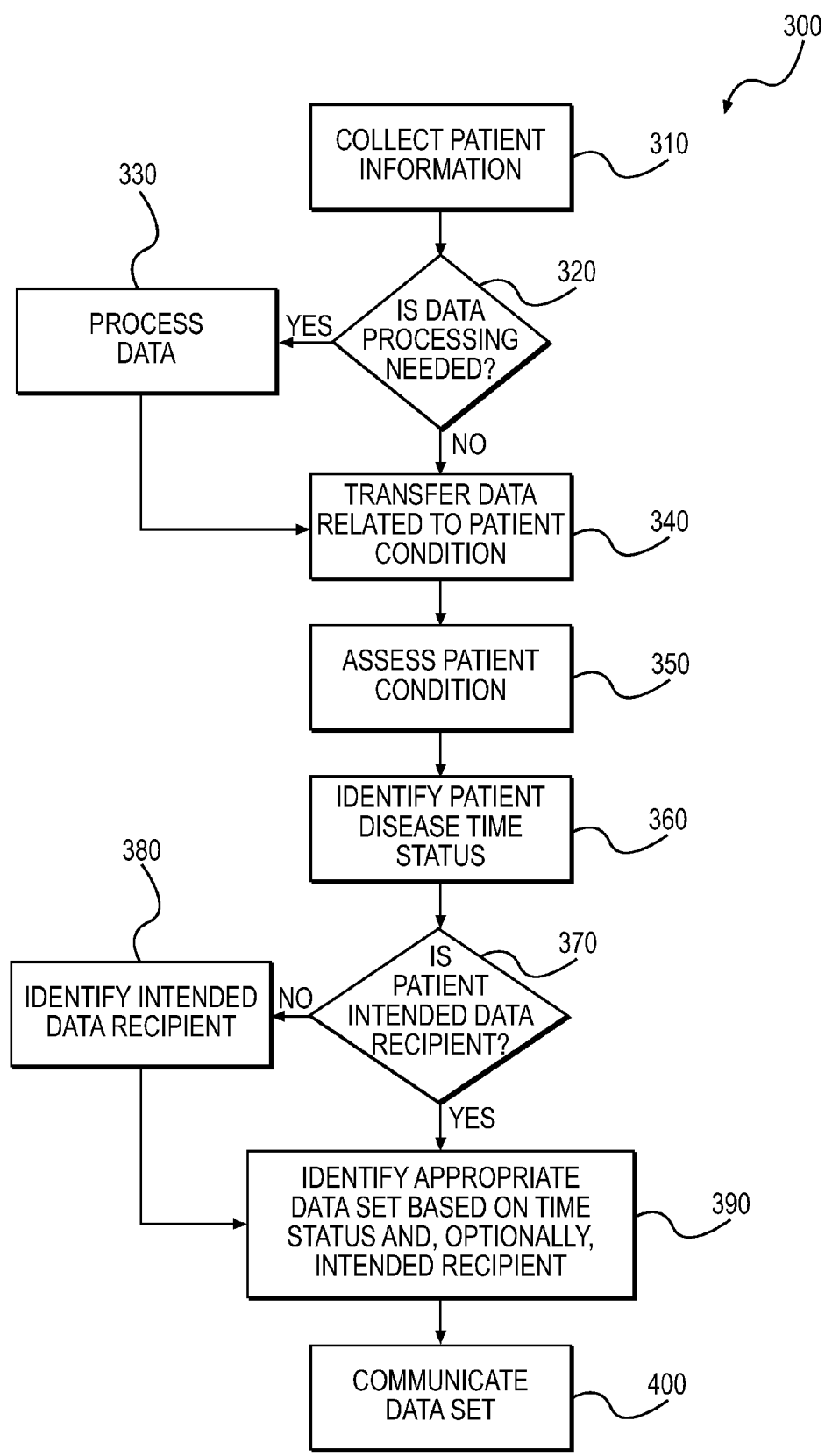
FIG. 3 illustrates methods for distributing healthcare information, according to certain embodiments.

FIG. 3 illustrates certain methods for distributing healthcare information, according to the methods and systems of the present disclosure. As noted previously, in some embodiments, the methods of the present disclosure can allow distribution of healthcare information based on a patient's condition, and over the time course of a patient's disease. The information delivered to the patient or others involved in the care of the patient can be based on the specific diseases or conditions, other medical factors, lifestyle factors, demographic factors, and the specific time status of a patient disease or condition, as described in more detail below. According to the method 300, information related to a patient condition is first collected, as shown at step 310. As indicated previously, the data may be collected via a variety of different data reception devices 14,18. Further, in some embodiments, the information may be collected directly from the patient and may include physiologic and health information acquired directly from a patient via a patient interface. In addition, the data may be collected from healthcare workers or others through a reception device 18, including a data entry interface.

Next, in some embodiments, the reception devices 14, 18 may process the data, if needed, before transferring the data to a data analysis system 20, as shown at steps 320 and 330. The data processing can include a number of suitable processing systems and algorithms. For example, in some embodiments, data processing may include converting one type of data into a format that is more easily stored, converted and/or analyzed. For example, the system may include analog-to-digital converters, or other systems configured to convert patient information to a digital format, or other format, that can be more easily analyzed or transmitted. In addition, the reception devices 14, 18 may further be configured to compress the data or eliminate irrelevant or otherwise uninteresting data before transferring the data for analysis.

Next, as shown at step 340, the data may be transferred to an analysis system 20 to assess the condition of a patient. As indicated above, the transfer may be conducted via any transfer process and may depend on the specific type of data or information being conveyed. Further, the information can be transferred using wireless means or any other suitable means to communicate between the reception devices 14, 18 and the analysis system 20.

Next, as shown at step 350 the specific condition of a patient may be assessed, as described in more detail below. The assessment may include, for example, the identification of a specific disease or condition encountered by the patient. Further, as described in more detail below, this assessment can include a number of other factors related to the specific disease or condition. In certain embodiments, the assessment can include a neuromarker, as described in detail in copending U.S. application Ser. No. 12/615,423, which is herein incorporated by reference in its entirety.

Next, as shown at step 360, after the patient condition is determined by the analysis system 20, the time status of a patient's disease is ascertained. As described in more detail below, in some embodiments, the time status of a particular patient may relate to a specific type of disease and the duration of the patient's involvement. Further, in some embodiments, once the patient's condition has been assessed and the time status of the patient's disease has been determined, the intended recipient of a data set is determined. For example, as shown at 370 the intended recipient of the disease is identified. Next, as shown at step 390, once the intended recipient of the data set is identified, an appropriate data set is identified to be distributed to the patient or others, and the data is communicated to the patient or other intended recipient, as shown at step 400. As described in more detail below, the communication of the data can be via a variety of different means and can be as a single step or performed sequentially.

Figure 4:
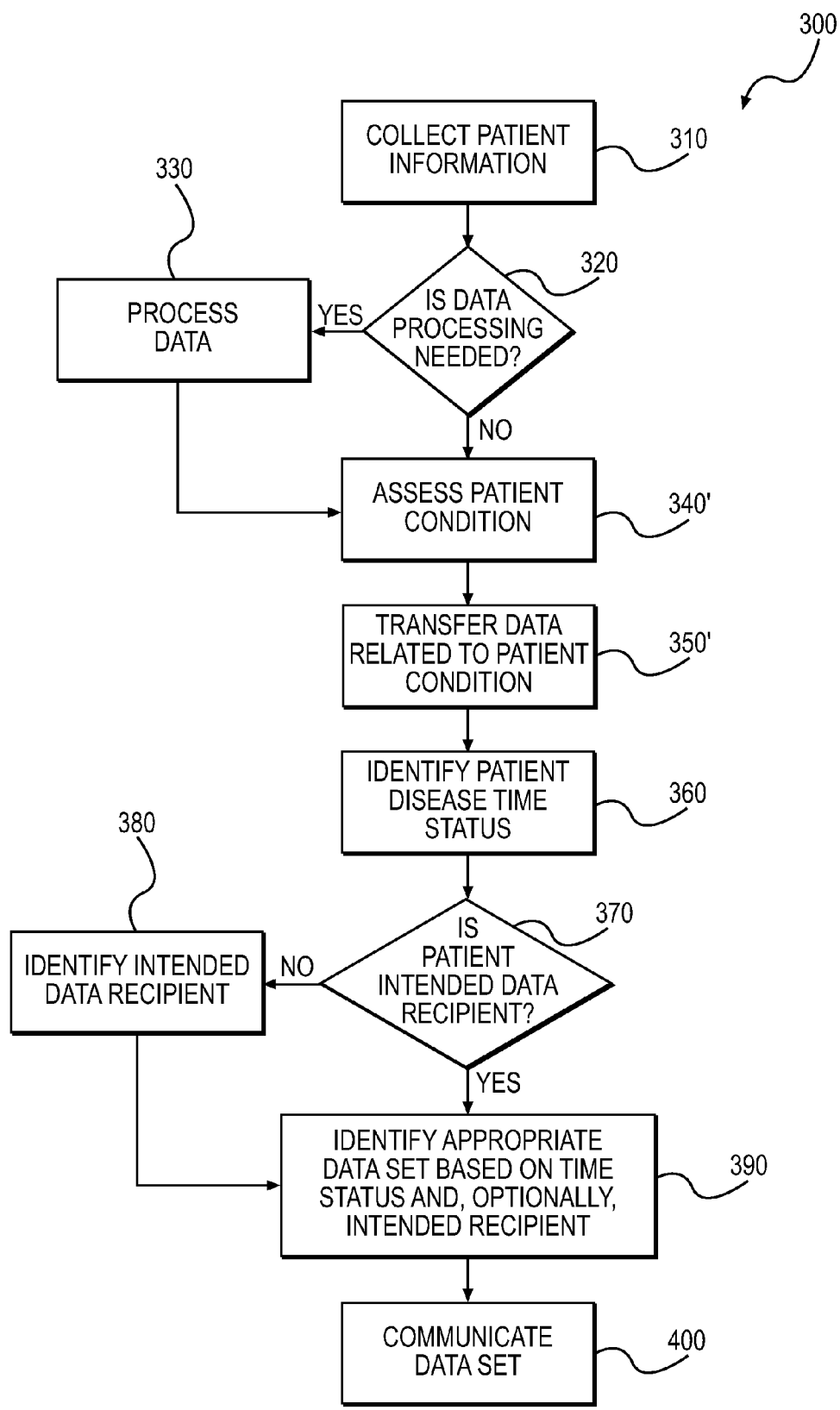
FIG. 4 illustrates certain embodiments of the methods of the present disclosure.

FIG. 4 illustrates certain embodiments of the methods of the present disclosure. As shown, according to the method of FIG. 4, the steps for identifying a data set to be communicated are similar to those described in FIG. 3. However, as shown, according to the method of FIG. 4, assessment of the patient's condition, as shown at step 340', can be performed before transfer of data related to the patient's condition to the analysis system, as shown at step 350'. In some embodiments, it may be desirable to perform an analysis of the patient's condition before transfer to the analysis system. In these embodiments, the determination of the patient's condition may be performed at the site of data acquisition and/or by the same system that collects the data related to the patient's condition. Further, as indicated previously, the reception devices 14, 18 may perform a portion of the data analysis, and the analysis system 20 may perform additional analysis.

Figure 5:
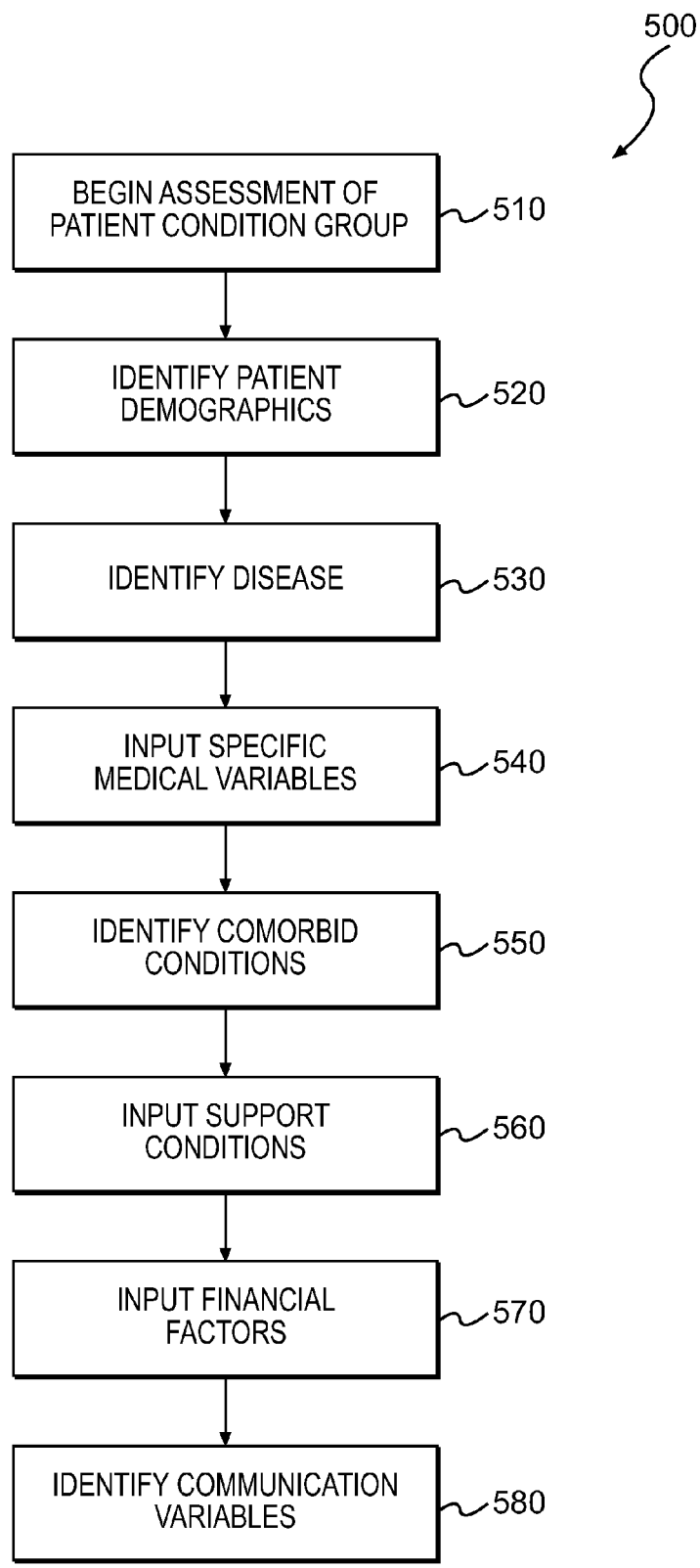
FIG. 5 illustrates methods for assessing and classifying a condition of a patient, according to certain embodiments.

As noted above, the assessment of the patient's condition can be based on a number of different factors. FIG. 5 illustrates certain methods for assessing a condition of a patient according to certain embodiments. As shown, the method 500 begins with processing of information in either the reception devices 14, 18 and/or the analysis system 20, as shown at step 510. Next, a variety of other additional information about the patient's condition, demographics, and other variables can be collected.

Next, as shown at step 520, information related to patient demographics may be collected. In some embodiments, the patient demographic information can include basic information including age, ethnicity, and family medical history. In addition, other basic information about the patient, including country of origin, place where the patient currently or has lived or traveled, and any other factor that may influence the types of diseases or medical condition to which the patient may be susceptible can be collected.

Next, as shown at step 530, the specific disease or condition may be identified. In some embodiments, the specific disease or condition may be determined based on an assessment input by either a physician, other healthcare worker, or medical diagnoses system. For example, in some embodiments, a medical diagnosis system, including a system configured to measure a physiological variable, may identify a specific disease or condition to which a patient may be susceptible or currently be suffering. For example, suitable physiological variables that may be measured may include, blood pressure, lab values, brain electrical activity, heart electrical activity, neuromuscular activity, and any other physiological variable that lends itself to medical diagnosis.

In other embodiments, information may be input into the analysis system 20 in order to identify conditions to which a patient may be susceptible but may not be currently suffering. For example, specific physiologic measurements, such as blood pressure, may be used to assist in assessment of conditions related to complications from abnormal or borderline physiologic measurements. For example, patients suffering from abnormal or high blood pressure may be at increased risk for cardiovascular disease, stroke, and other medical conditions. Therefore, in some embodiments, any of these conditions may be used in an assessment of a patient's condition to identify potential risk factors and assist in identifying patient data sets related to information that may be helpful in preventing future complications or progression of disease related to these physiologic variables. The measurements, once analyzed, can also predict the onset of the next stage of disease and provide an approximation of the likely duration of current stage, for example in cancer patients.

Next, information related to a patient's specific medical condition can be ascertained by collecting patient specific medical variables, as shown at step 540. There are a number of factors that can be considered as patient specific medical variables. For example, in one embodiment, information related to the acute nature or chronic nature of the disease can be ascertained. In some embodiments, it may be desirable to determine whether or not a disease is a chronic condition that can lead to severe medical complications itself or whether the disease is simply one variable that can predispose a patient to more severe medical conditions. For example, a number of diseases are considered chronic conditions that predispose patients to more severe medical conditions. Such chronic conditions can include, for example, high blood pressure, diabetes, abnormal cholesterol, abnormal lipids, and a variety of other metabolic and laboratory abnormalities that may affect a patient's overall health.

In some embodiments, it may be desirable to identify conditions that are more acute. More acute conditions can include conditions that may cause severe medical problems and/or death in the short term. Such conditions may include more advanced metabolic conditions, cardiovascular disease, advanced or acute kidney disease, liver disease, cancer, and various other medical conditions that can cause severe health problems and/or death. Overall, the assessment of the patient's condition and the determination of the time status of the patient's conditions can be related to the specific disease or condition that a patient has encountered and the chronicity of the disease or condition.

In some embodiments, the specific medical variables related to the patient's condition can include treatments that the patient is undergoing. For example, various prescription drugs or other treatments that the patient undergoes can impact the information the patient may wish to receive during the time course of the patient's condition. Many medications are known to cause significant side effects, and, therefore, the information the patient should receive can be dependent upon the specific medical treatments that the patient is receiving. In addition, knowledge of the specific medical treatments that the patient is receiving may be important to identify alternative medical treatments if the current treatments are not effective or if the side effects from the current treatments are undesirable. Accordingly, in some embodiments, the systems of the present disclosure assist in identifying current treatments, assessing their effectiveness, and recommending or identifying possible alternative or additional treatments, if desired.

In some embodiments, the specific medical variables related to the patient's disease can include hereditary or genetic factors related to the disease. Hereditary or genetic factors can be important to determine the type of information that may be important to the patient over the time course of the disease or condition. In some cases, the hereditary of genetic factors can be important so that the patient or other people involved in the patient's care can be informed of genetic factors related to the disease. In addition, the genetic factors can be important for informing life decisions, such as, child bearing and parenthood. Further, genetic factors related to the disease can help inform treatment decisions, especially in cases in which genetic factors may indicate that the patient's predecessors had suffered from the disease. In such cases, understanding the genetic factors may be important for informing the patient of possible future complications and viable treatment options for that patient.

Next, comorbid conditions for the specific patient may be identified, as shown in step 550. Identification of the comorbid conditions can be important. For example, with chronic conditions such as diabetes, understanding comorbid conditions that may affect treatment options and/or complications related to the disease or condition can affect the medications that the patient may take and may be indicative of the advancement of the disease state.

Next, as shown at step 560, patient support conditions and/or family relationships may be ascertained. Generally, patient support conditions can be understood to mean any social or familial support situations that the patient may have. Availability of support groups and family relationships during certain disease or conditions can be important for assisting patients with activities of daily living, administration of medication, and care of severely ill patients. Therefore, in some embodiments, patient support conditions may be ascertained in order to determine types of information and/or data sets that may be communicated to particular patients. For example, patients who have access to continual care and/or at home support from family members may be in less need of assistance from outside nurses aids or other care, and, therefore, may not be in need of the same type of information related to outside additional assistance as other patients. Further, patients who are not yet engaged with various support groups for certain disease or conditions may desire information regarding such groups, and, therefore, knowledge of such relationships can be important for determining a data set for communication to such patients.

In addition, collection of additional information related to financial factors and communication variables can be important for some patients, as shown in steps 570 and 580. How a patient funds their medical care, and whether or not they are able to fund certain types of care, can be important in determining what information should be presented to such patients. In addition, the ability of patients to receive such information and comprehend such information may be an important communication variable. Therefore, in some embodiments, it may be desirable to collect financial information, insurance information, information regarding the ability of patients to use various communication resources, including, for example, audio and visual resources, computer systems, written or audio materials, or other types of communication systems. Any information related to patient financial information and ability of patients to receive certain types of information may be collected.

Figure 6:
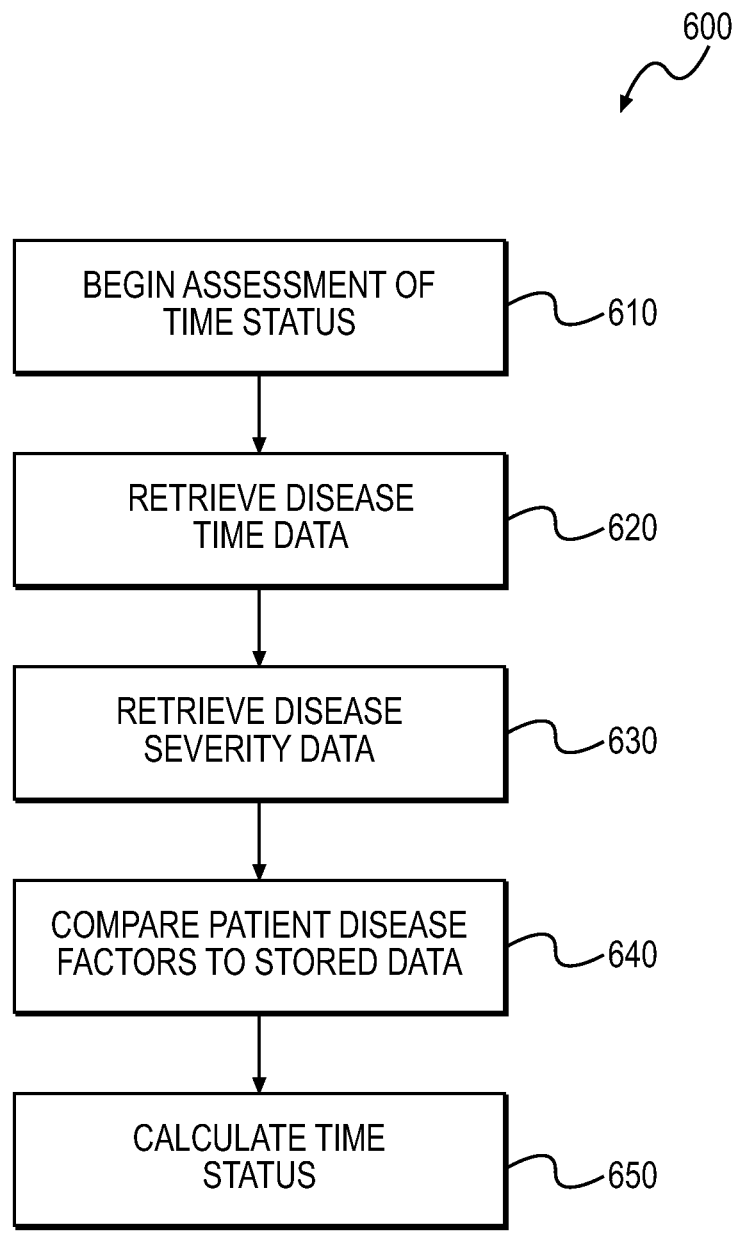
FIG. 6 illustrates methods for assessment of a time status of a condition of a patient, according to certain embodiments.

In some embodiments, after assessment and classification of the patient disease or condition, the time status of the patient's disease or condition may be assessed. FIG. 6 illustrates methods for assessment of a time status of a disease state of a patient, according to certain embodiments. The method 600 begins at step 610 when information related to the patient's disease or condition is received by an analysis system 20. Next, the analysis system 20 will retrieve disease time data, as shown at step 620. In some embodiments, disease time data can include a variety of factors related to the patient's specific disease or condition. For example, when a patient's specific disease or condition has been identified, information related to the development and progression of that disease or condition can be retrieved from the data base. A variety factors can be considered to relate to time data of the particular disease or condition. For example, information related to the time data of the disease can include the specific type of disease, the general life expectancy of a person having that disease at a certain age, the rate of progression of the disease for certain patient populations, various known clinical stages of the disease, as categorized by known clinical factors, and other disease staging criteria.

Next, as shown at step 630, data related to disease or condition severity can be ascertained. In some embodiments, disease severity criteria can include known clinical stages for particular diseases, various types or sub-types of diseases, known treatment types and resistance to certain treatments, or other indicators of disease severity.

Next, as shown at step 640, the patient specific disease factors can be compared to disease time data and disease severity data, as previously retrieved. In some embodiments, the patient's disease time status can be determined based on a specific disease stage or severity of the disease, based on that particular patient's disease profile, as ascertained by physiologic measurements or other relevant information, or compared to a cohort of patients in the database with similar physiologic or symptom-based assessments. For example, a patient's disease state can include the level of progression of disease or condition indicated by disease specific variables. For example, for certain empirically measureable diseases such as hypertension, the disease time status can be calculated based on the level of hypertension or the measurement of the blood pressure. In some embodiments, the disease time status can be indicated based on the degree of the progression or spread of the disease. For example, for a disease such as cancer, the disease time status may be indicated by the level of disease progression to other parts or the body or the level of disease growth in a particular area of the body. Various known disease staging categories are available and can be based on the specific disease or condition. Further, prediction about the likely length of time of the current stage, and prediction about the degree and timing of onset of next stage of disease may be ascertained based on one or more of the aforementioned measurements or assessments. In various embodiments, the predictions can be based on data from the specific patient, based on a comparison with a single other patient or a group of patients, or based on normative data from the entire population of patients represented in a comparative data set.

Figure 7:
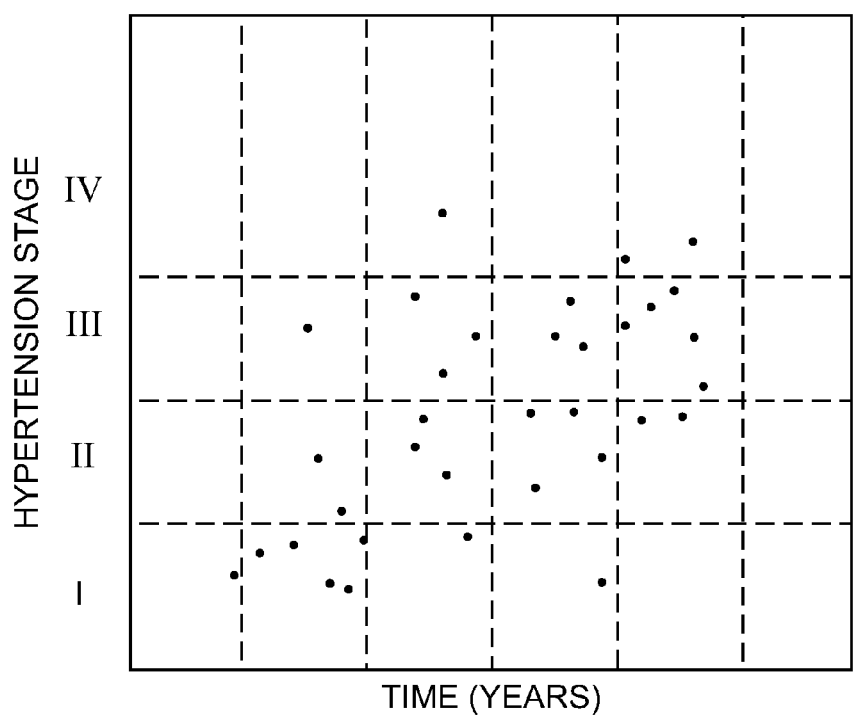
FIG. 7 illustrates methods for determining a time status for patients with certain diseases.

In addition, for a more chronic condition that can lead to long-term consequences, but in itself may not cause immediate problems, the time period during which the patient suffers from the disease can be ascertained to determine the time status of the disease. For example, FIG. 7 illustrates methods for categorizing a disease stage for a patient with hypertension. As shown in FIG. 7, the disease stage or level of hypertension is graphed on the Y access and the time period during which the patient has suffered from the disease is graphed on the X access. Patients may be grouped based on the amount of time during which they have suffered from the disease or condition, and also the stage of the particular disease or condition. Patients may therefore be grouped within various categories to ascertain the type of information that may be desirable for patients based on the severity of the disease or condition and based on the time during which they have suffered from the disease or condition.

Such classification systems may be desirable for a number of reasons. In some embodiments, it may be desirable to assist patients suffering from a chronic condition such as hypertension in order to prevent more long-term complications. Therefore, in some embodiments, patients who have not been suffering from hypertension for a long time, or who have low levels of hypertension for some time, may be interested in life-style changes or certain medications to lower the degree of hypertension and prevent complications. In some embodiments, patients who have more severe hypertension or have suffered for a longer period of time may be interested in information related to more aggressive treatments or information related to more severe side effects from hypertension.

Figure 8:
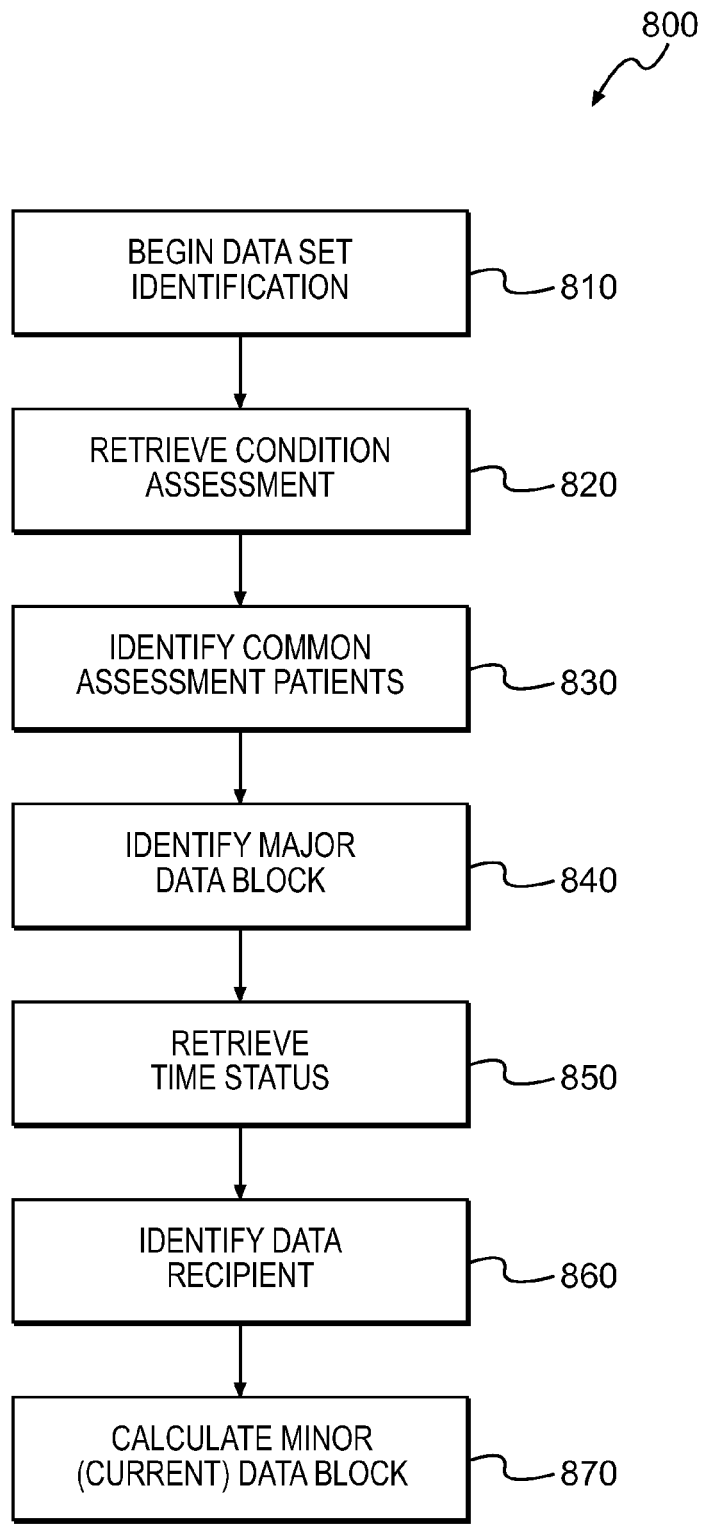
FIG. 8 illustrates methods for identifying data sets to be communicated to a patient or other individuals, according to certain exemplary embodiments.

After the specific disease or condition for a patient is identified and the time status of the patient's condition is ascertained, a data set that is to be communicated to the patient or other individuals is identified. FIG. 8 illustrates methods for identifying the data set to be communicated to a patient or other individuals, according to certain exemplary embodiments. As shown, the method 800 of FIG. 8 begins with step 810 wherein the time status and the disease information are transmitted to the analysis system 20. Next, as shown at step 820, the analysis system retrieves the information related to the disease condition assessment, as previously determined. Then, as shown as step 830, the analysis system 20 identifies a common cluster or group of patients having a similar disease or condition assessment. Patients having a similar disease or condition are assigned a major data block, as indicated at step 840. In some embodiments, the major datablock includes a large group of information potentially of interest to these patients.

In some embodiments, the major data block can be a data set selected based on the patient's disease classification. For example, in some embodiments, the database can include datasets identified as potentially interesting to all patient's suffering from, at risk for, or involved with the care of patients having a particular disease. The particular disease can include any particular medical, psychiatric, surgical, or other condition, as described with respect to Step 520 above. Further, in some embodiments, the major data set can be based on a more specific disease condition assessment, as identified through the steps indicated in FIG. 5 above.

Next, the patient time status and intended recipients are retrieved, as shown at steps 850 and 860, and based on this criteria, a minor data block is identified, as shown at step 870. In some embodiments, the minor data block is a subset of the major data block based on specific patient time stats and the intended recipient.

The minor data block can be selected as a subset of the major data block. For example, in some embodiments, the minor data block is selected based on the intended recipient of the information and/or the time status of a patient's condition. For example, in some embodiments, a patient who is newly diagnosed with a disease or condition is assigned a major data block, as indicated above. Then, as the time of diagnosis, the time status of the patient's condition is assessed, and multiple minor data blocks are selected to be communicated to one or more different recipients. For example, in one embodiment, a newly diagnosed patient is assigned a major data block, and a minor data block is selected to be communicated to that patient based on the time status of the patient at diagnosis. In addition, one or more additional minor data blocks may be selected to be communicated to other recipients, including family members, coworkers, and/or healthcare personnel, for example. Further, at subsequent times, the times status of a patient's condition can be reassessed, and new or additional minor datablocks may be selected for communication to patients or others. The new or additional minor datablocks can again be subsets of the same major datablock, but may include different information than the previous minor datablocks based on the updated time status of the patient's condition.

In addition, in some embodiments, as indicated above, the data stored in the database 28 can be updated and/or changed. Therefore, the major and minor datablocks that may be selected can be changed as new information becomes available. In addition, in some embodiments, the time status of a patient's disease can be based, in part, on the time since diagnosis, the severity of the disease, and/or the information previously communicated to the patient (e.g., which data of a major data set has been communicated). Therefore, although some patient's may be diagnosed with a disease at differing stages of severity, the time status for each patient may be determined based on not just the particular clinical variables of the patient's condition, but also the amount of information or experience that the patient or others have with the disease. Similarly, the minor data block, being determined partly based on the time status of the patient's condition and the intended recipient of the information, is selected based on the patient's information previously communicated to the patient or others, the time during which the patient has experienced the condition, and information previously received by the intended recipient.

Other embodiments will be apparent to those skilled in the art from consideration of the specification and practice of the devices and methods disclosed herein. It is intended that the specification and examples be considered as exemplary only, with a true scope being indicated by the following claims. A number of patents, patent publication, and nonpatent literature documents have been cited herein. Each of these documents is herein incorporated by reference.

What is claimed is:

1. A method for communicating health information by a communication system comprising an analysis system, implemented by one or more processors, the method comprising:
    collecting patient information associated with a patient, by one or more reception devices, wherein the patient information comprises physiological information related to a health condition of a patient;
    processing, by the analysis system, the physiological information to assess the health condition associated with the patient;
    determining, by the analysis system, a time status of the patient's condition;
    assigning, by the one or more processors, a major data block to the patient based on the health condition associated with the patient, wherein the major data block includes;
        information that is identified as relevant to all patients who have the health condition or are at risk for the health condition, and
        minor data blocks, which are subsets of the major data block and comprise information that is identified as potentially relevant to a subset of the patients who have the health condition or are at risk for the health condition;
    selecting, by the one or more processors, a plurality of minor data blocks from the major data block based on the time status of the health condition and an intended recipient of the minor data block, wherein each of the plurality of minor data blocks is intended for a different recipient; and
    communicating, by the communication system, each minor data block as a data set to the intended recipient of each minor data block.

2. The method of claim 1, wherein collecting patient information includes performing at least one of either a diagnostic test and entry of data into a data interface.

3. The method of claim 2, wherein performing the diagnostic test includes collecting data related to brain electrical activity.

4. The method of claim 1, further including transmitting the data set to a location distant from the analysis system.

5. The method of claim 1, wherein [selecting at least one of the plurality of minor data blocks includes comparing the health condition of the patient to health conditions of other patients represented by data stored in a database and selecting the minor data block based on the comparison] assignment of the major data block includes classifying the patient condition relative to the condition of other patients represented by data stored in a database.

6. The method of claim 5, wherein the assignment is based on at least one of a stage of disease progression, a life expectancy of the patient, a comorbid condition, a treatment received by the patient, and a genetic profile of the patient's condition.

7. The method of claim 1, wherein the data set communicated to one of the intended recipients includes at least one therapeutic recommendation.

8. The method of claim 1, wherein the data set communicated to one of the intended recipients includes a prediction of a length of time remaining in a current disease stage.

9. The method of claim 1 wherein the data set communicated to one of the intended recipients includes a prediction of a time of onset of a next disease stage.

10. The method of claim 1, wherein the data set communicated to one of the intended recipients includes a prediction of a severity of a next disease stage.

11. The method of any one of claims 8-10, wherein the prediction is based on the patient's individual measurements and self-normed baseline.

12. The method of any one of claims 8-10, wherein the prediction is based on data from a single patient or group of patients with similar measurements.

13. The method of any one of claims 8-10, wherein the prediction is based on a population norm of other patients represented by data stored in a database.

14. The method of claim 1, wherein the patient information further comprises at least one of information related to patient support conditions, patient financial information, insurance information, and ability to receive certain types of information of the patient.

15. The method of claim 1, wherein selecting the minor data block is based on information from the major data block which has been previously communicated to the patient.

16. The method of claim 1 wherein the intended recipients include the patient and a doctor treating the patient.

17. The method of claim 16 wherein the intended recipients include at least one of family member of the patient, social worker, peer support group, and healthcare personnel outside the setting of a clinic or hospital.

* * * * *